US00PP25867P3

(12) United States Plant Patent
Larse

(10) Patent No.: US PP25,867 P3
(45) Date of Patent: Sep. 8, 2015

(54) STRAWBERRY PLANT NAMED 'CRYSTALINA'

(50) Latin Name: *Fragaria×ananassa*
Varietal Denomination: Crystalina

(71) Applicant: Sweet Darling Sales, Inc., Aptos, CA (US)

(72) Inventor: John Larse, Aptos, CA (US)

(73) Assignee: Sweet Darling Sales, Inc., Aptos, CA (US)

( * ) Notice: Subject to any disclaimer, the term of this patent is extended or adjusted under 35 U.S.C. 154(b) by 27 days.

(21) Appl. No.: 13/986,676

(22) Filed: May 23, 2013

(65) Prior Publication Data

US 2013/0340136 P1 Dec. 19, 2013

Related U.S. Application Data

(60) Provisional application No. 61/650,798, filed on May 23, 2012.

(51) Int. Cl.
*A01H 5/00* (2006.01)
*A01H 5/08* (2006.01)

(52) U.S. Cl.
USPC ..... Plt./209
CPC ..... *A01H 5/0893* (2013.01)

(58) Field of Classification Search
USPC ..... Plt./209
See application file for complete search history.

*Primary Examiner* — Annette Para
(74) *Attorney, Agent, or Firm* — Cooley LLP

(57) ABSTRACT

The present invention relates to new and distinct day-neutral strawberry variety designated as 'CRYSTALINA' (a.k.a. '107936').

15 Drawing Sheets

Latin name of genus and species: *Fragaria×ananassa.*

Varietal denomination: 'CRYSTALINA' (a.k.a. '107936', or 'CRYSTAL' previously).

BACKGROUND OF THE INVENTION

'CRYSTALINA'

The present invention relates to a new and distinct early day-neutral strawberry variety designated as 'CRYSTALINA' (a.k.a. '107936', or 'CRYSTAL' previously). This new variety is the result of a controlled-cross between a female parent cultivar designated '103904' and a male parent cultivar designated '103926' (both unpatented, proprietary cultivars) made by the inventor and first fruited in Watsonville, Calif. growing fields.

Following selection and during testing, the plant was originally designated '107936' and subsequently named 'CRYSTALINA'. The new variety of 'CRYSTALINA' was asexually reproduced via runners (stolons) by the inventor at Watsonville, Calif. Asexual propagules from the original source have been tested in the Watsonville growing fields and, to a limited extent, growing fields in low and high elevation. The properties of this variety were found to be transmissible by such asexual reproduction. The cultivar is stable and reproduces true to type in successive generations of asexual reproduction.

SUMMARY OF THE INVENTION

'CRYSTALINA'

This invention relates to a new and distinctive early producing day-neutral type cultivar designated as 'CRYSTALINA'. It is primarily adapted to the climate and growing conditions of the central coast of California. This region provides the necessary temperatures required for it to produce a strong vigorous plant and to remain in fruit production from April through October. The nearby Pacific Ocean provides the needed humidity and moderate day temperatures and evening chilling to maintain fruit quality for the production months.

The following traits in combination distinguish strawberry variety 'CRYSTALINA' from the known strawberry varieties. Plants for the botanical measurements in the present application were grown as annuals. In the following description, color references are made to The Royal Horticultural Society Colour Chart, 1995 Edition, except where general terms of ordinary dictionary significance are used.

The following are the most outstanding and distinguishing characteristics of this new variety when grown under normal conditions in Watsonville, Calif.

Large fruit; and

High yield.

When 'CRYSTALINA' is compared to the proprietary female parent '10394', 'CRYSTALINA' has larger leaflets and larger fruit. 'CRYSTALINA' strawberries are more resistant to weather changes and do not bruise as easily as the female parent.

When 'CRYSTALINA' is compared to the proprietary male parent '103926', 'CRYSTALINA' is similar in most aspects save for having higher yield.

When 'CRYSTALINA' is compared to 'Albion' (U.S. Plant Pat. No. 16,228), 'CRYSTALINA' produces hardier plants and a higher yield in berries.

DESCRIPTION OF THE DRAWINGS

The accompanying color photographs depict various characteristics of the 'CRYSTALINA' cultivar at various stages of development as nearly true as possible to make color reproductions.

DETAILED BOTANICAL DESCRIPTION

'CRYSTALINA'

Figure 1:
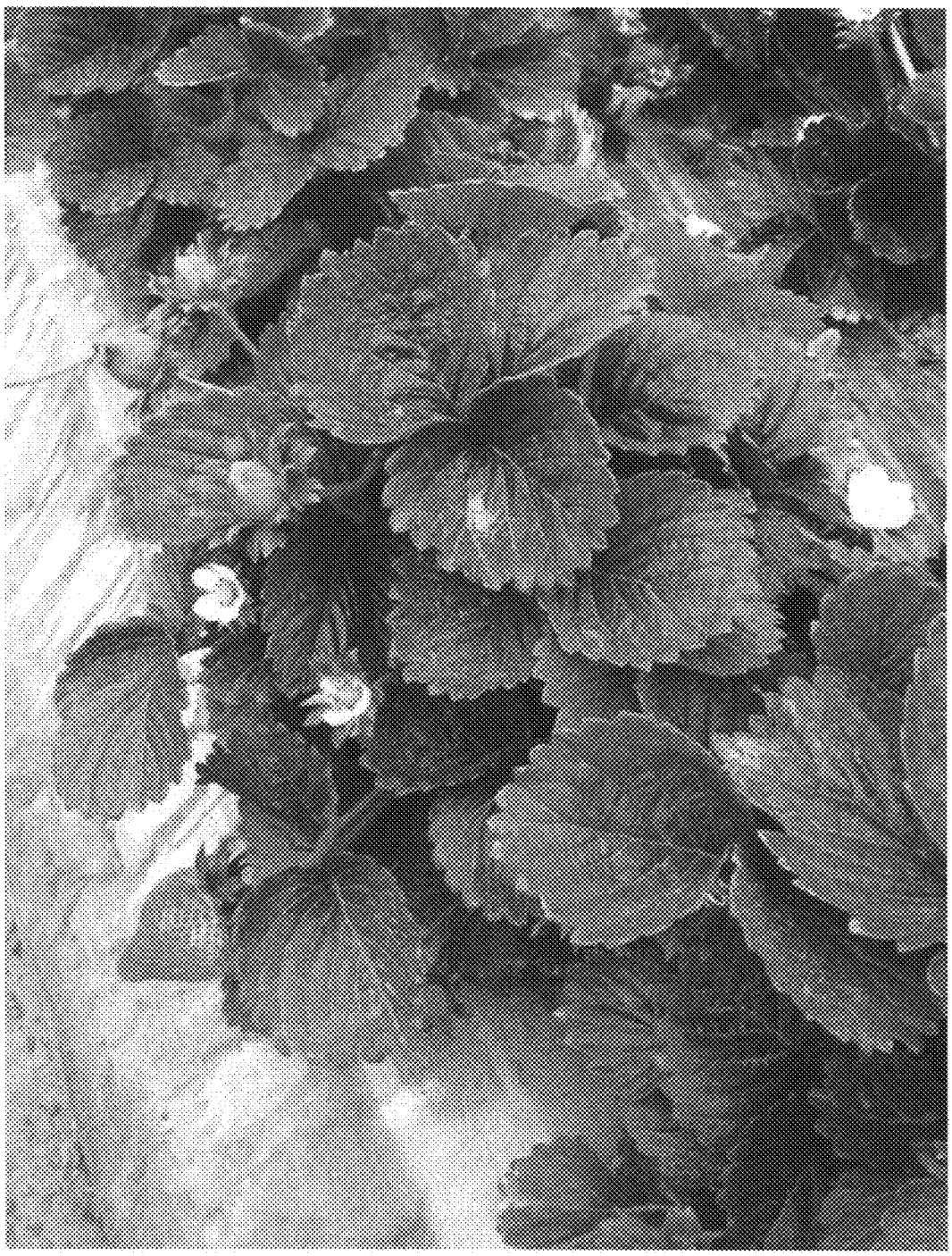
FIG. 1 shows 'CRYSTALINA' plant in early May.
Figure 2:
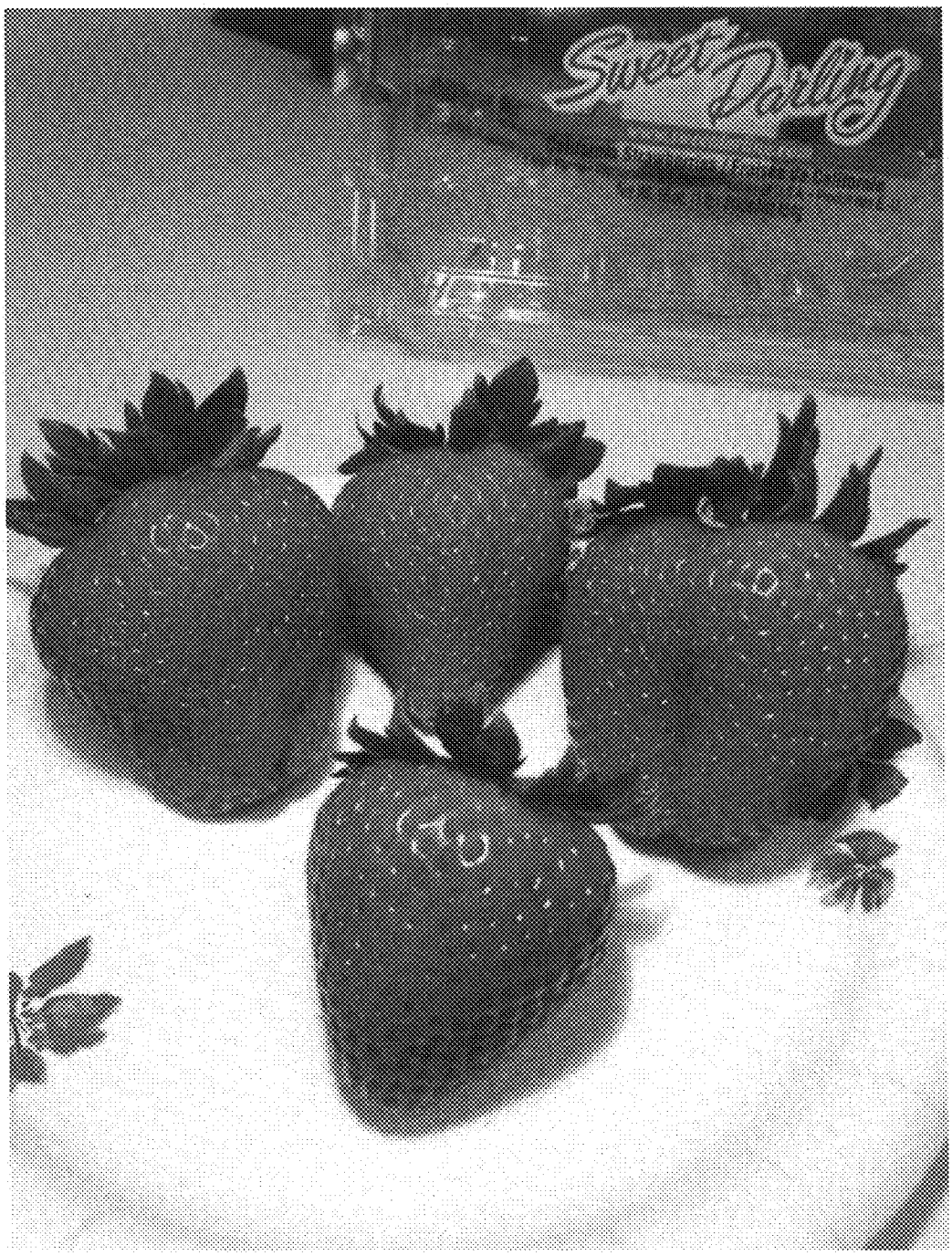
FIG. 2 shows 'CRYSTALINA' strawberries from early May picking.
Figure 3:
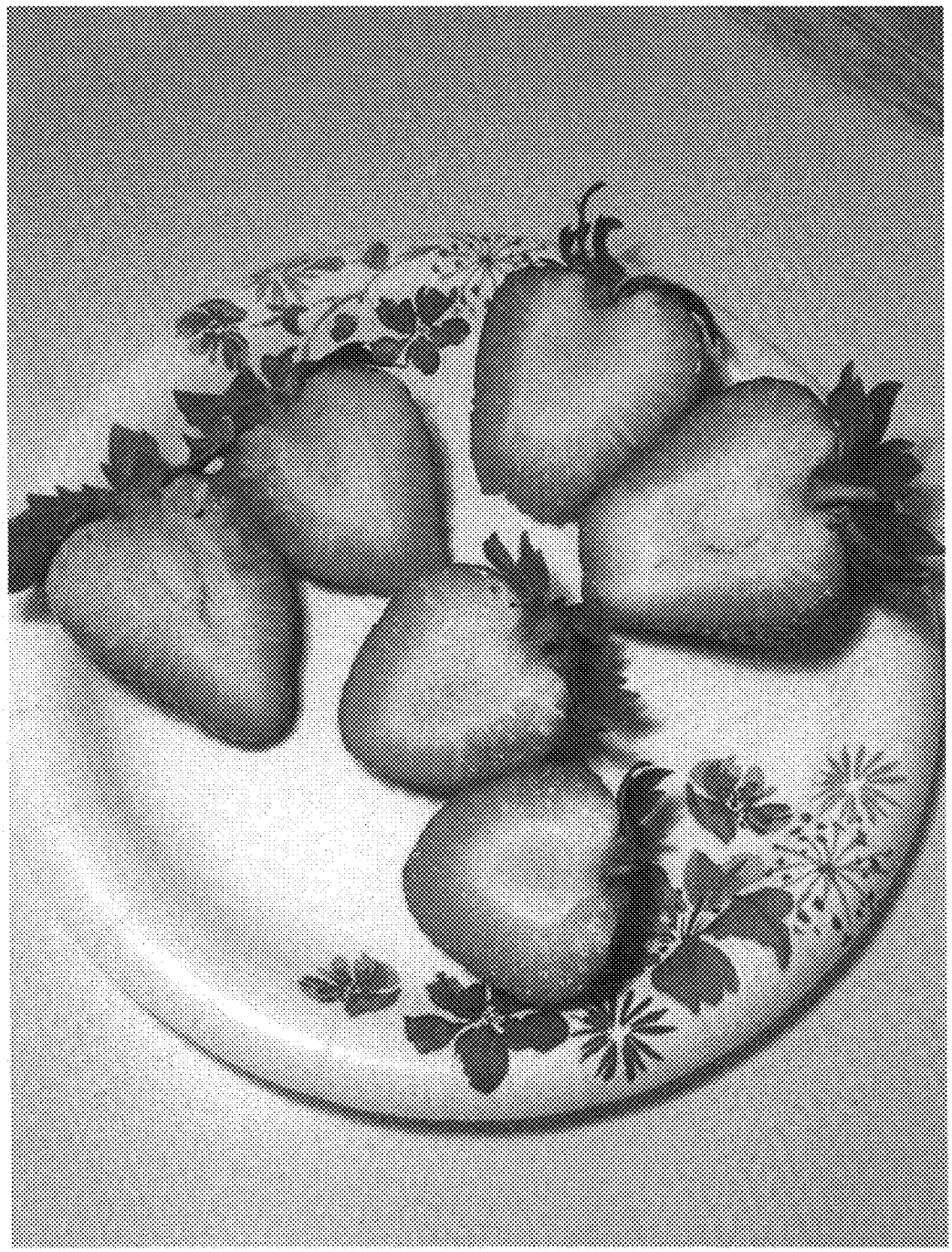
FIG. 3 shows Cross section of early May 'CRYSTALINA' strawberries.
Figure 4:
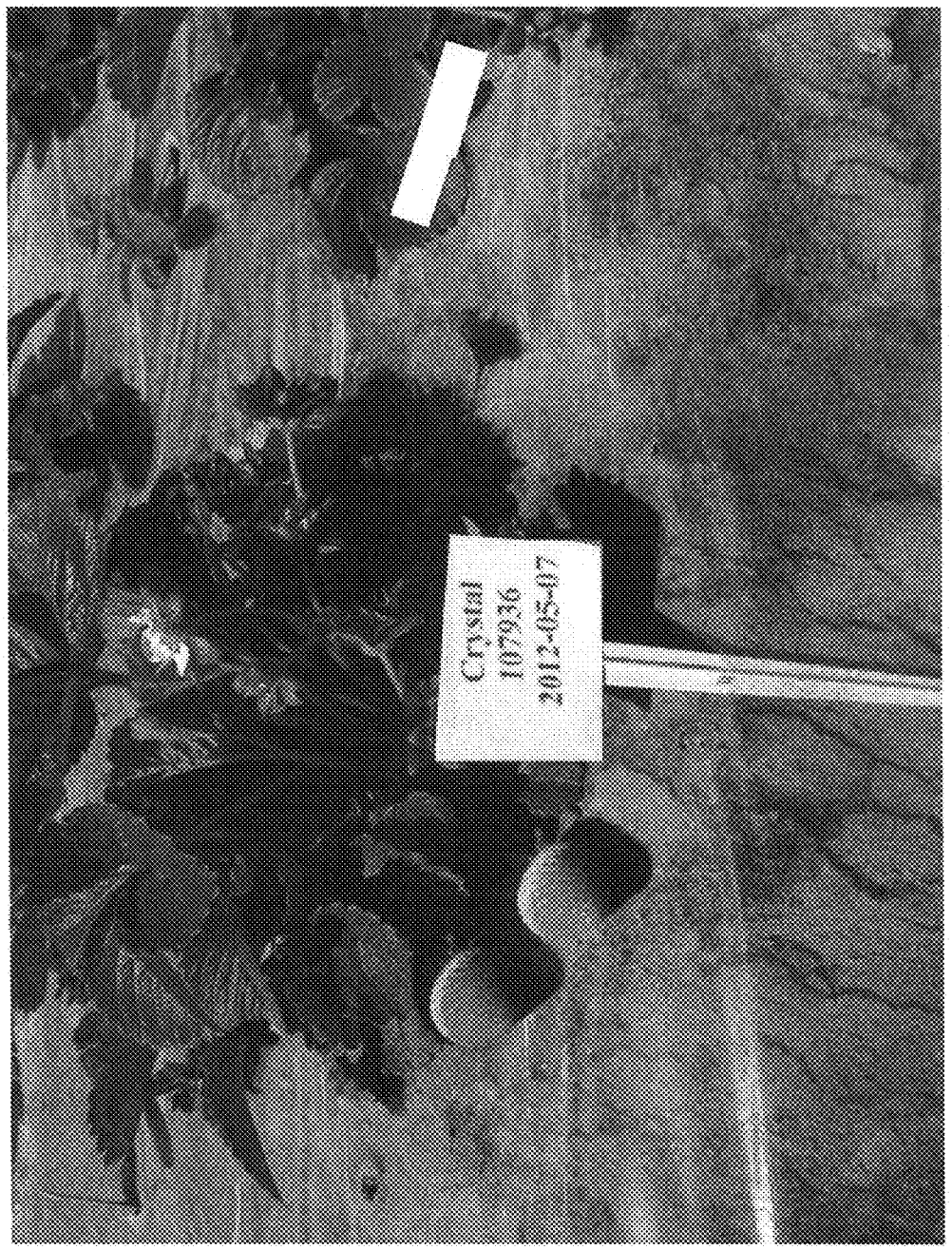
FIG. 4 shows ripe and near-ripe fruits of 'CRYSTALINA' in May.
Figure 5:
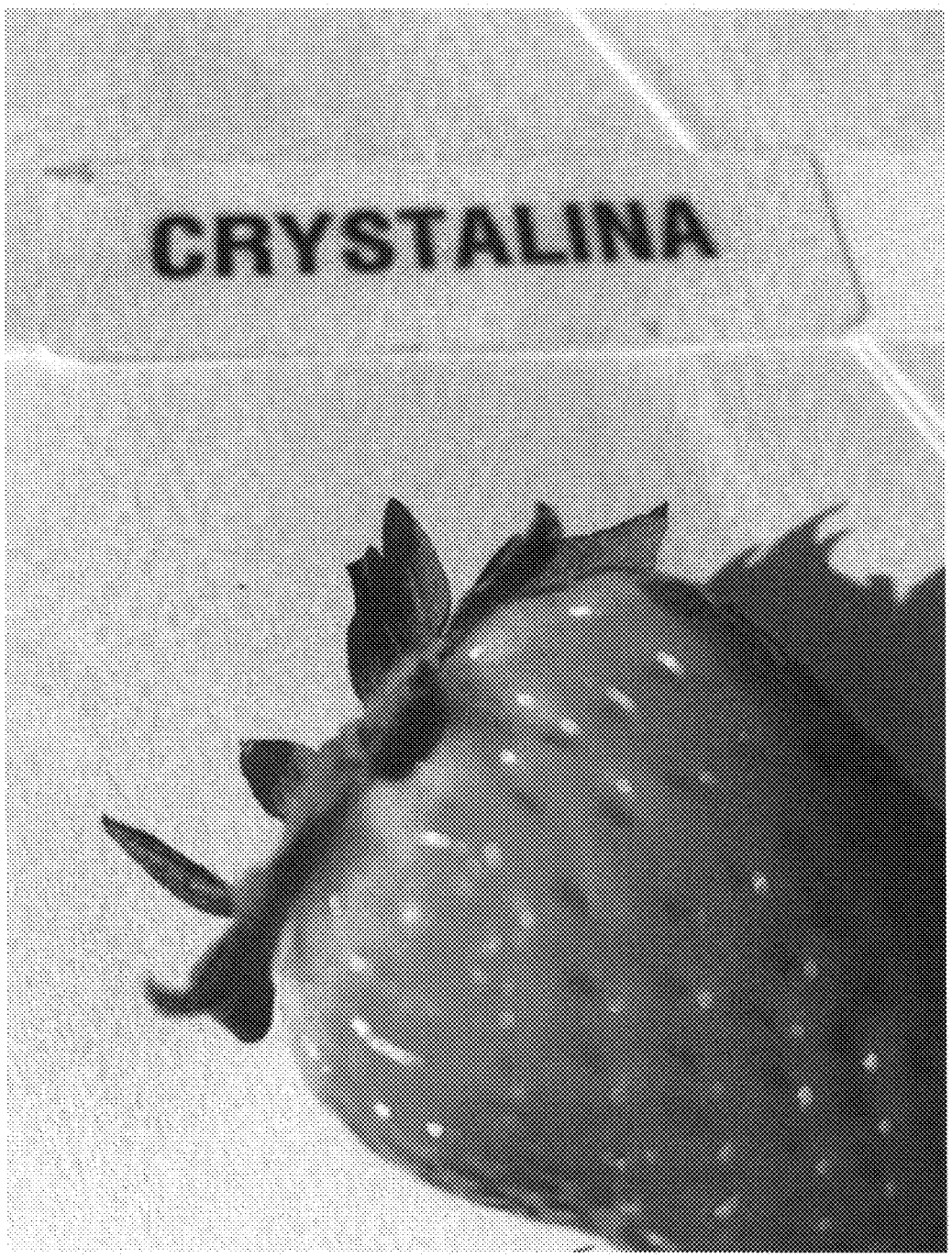
FIG. 5 shows a nearly ripe 'CRYSTALINA' achene.
Figure 6:
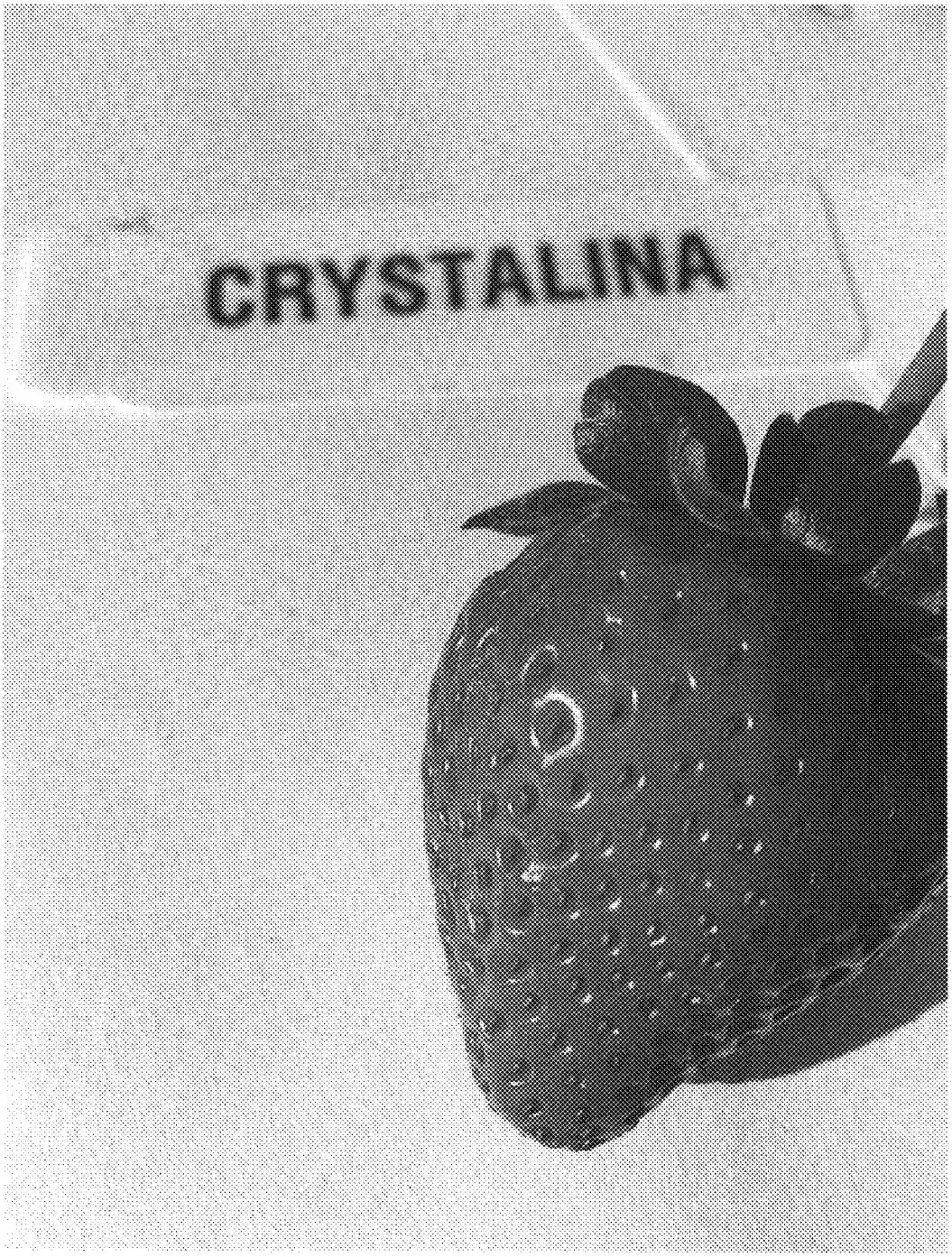
FIG. 6 shows a ripe 'CRYSTALINA' achene.
Figure 7:
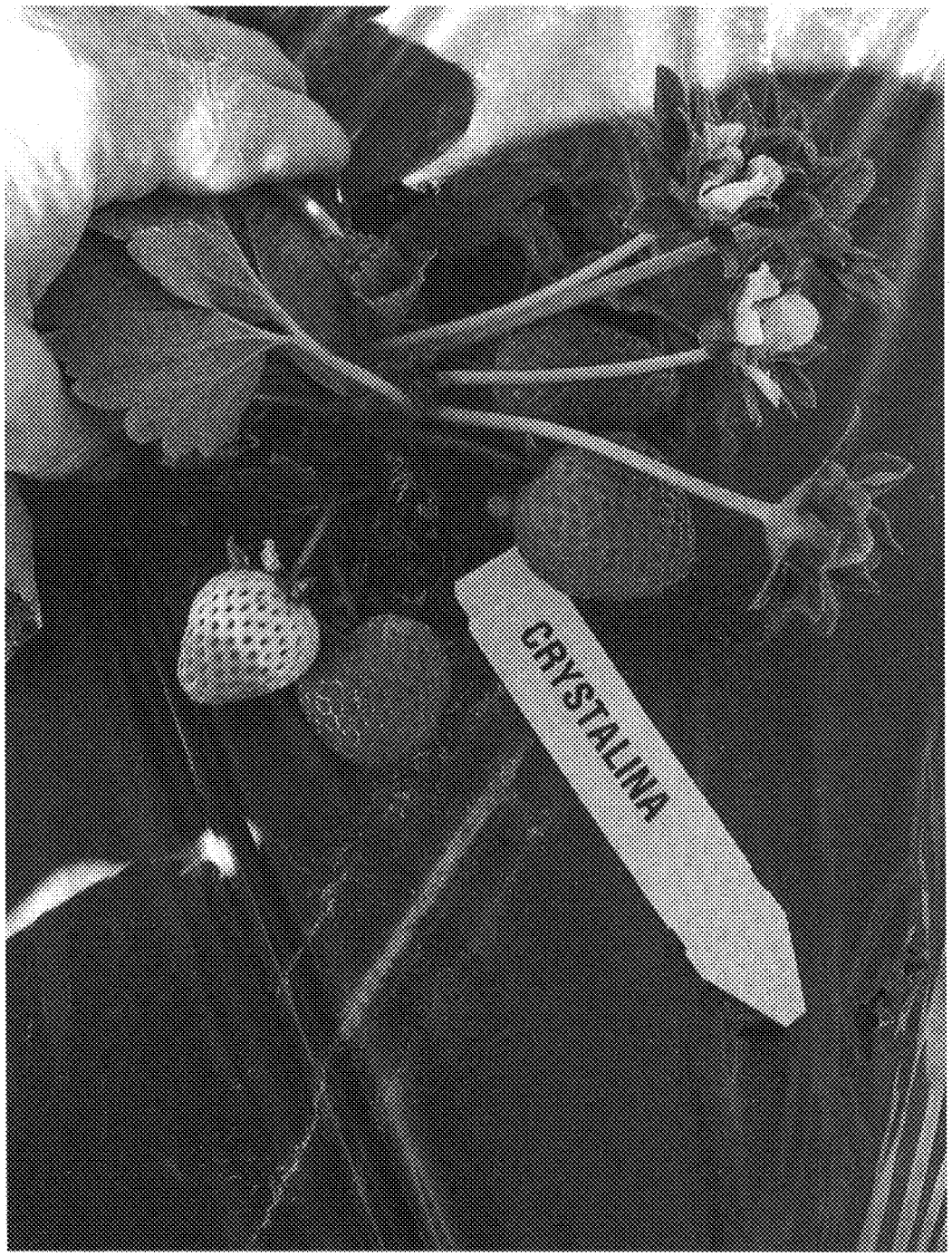
FIG. 7 shows a first crown of a 'CRYSTALINA' florescence.
Figure 8:
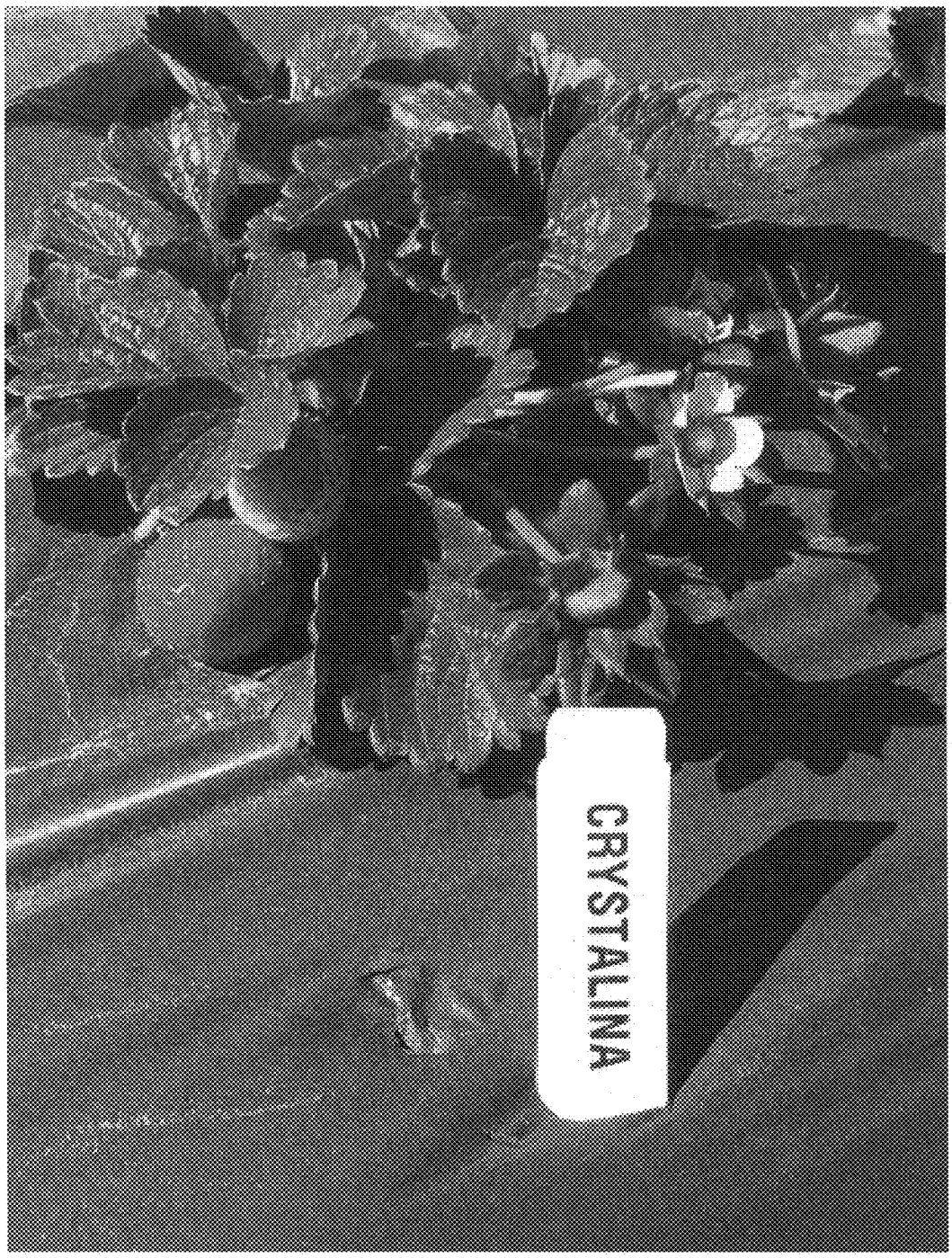
FIG. 8 shows a unitary apical florescence of 'CRYSTALINA' with concave, overlapping leaflets.
Figure 9:
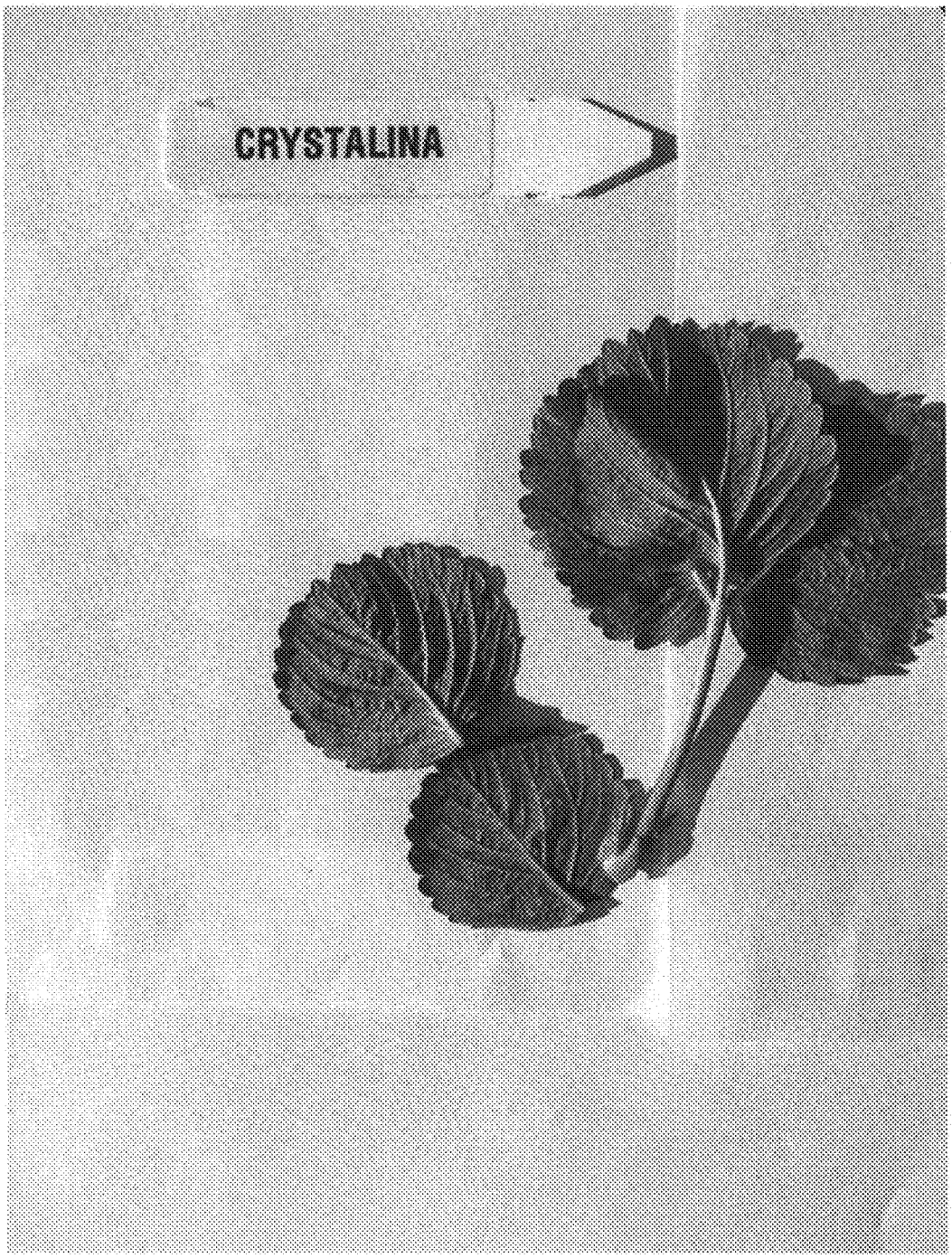
FIG. 9 shows a 'CRYSTALINA' leaflet.
Figure 10:
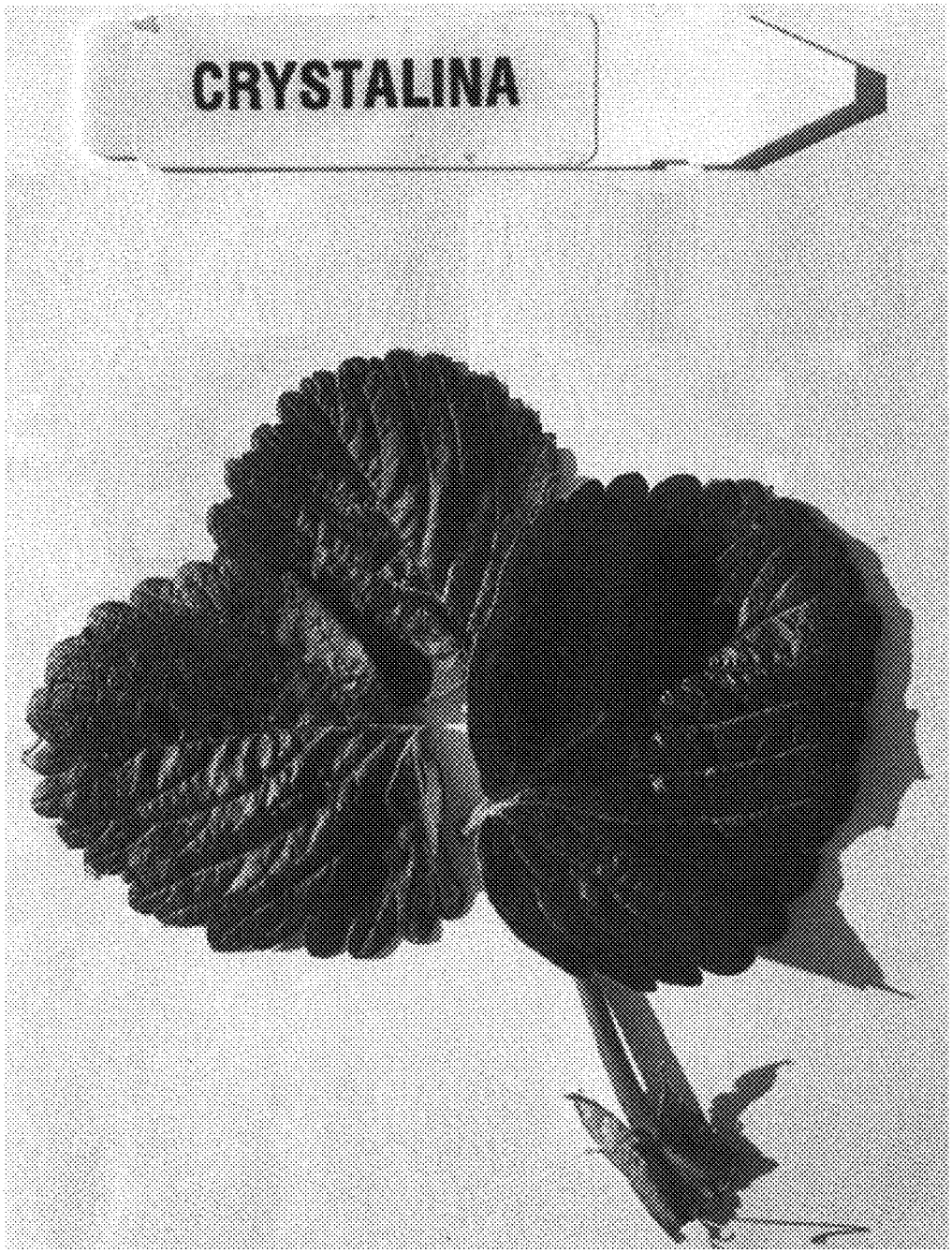
FIG. 10 shows the topside of a 'CRYSTALINA' leaflet.
Figure 11:
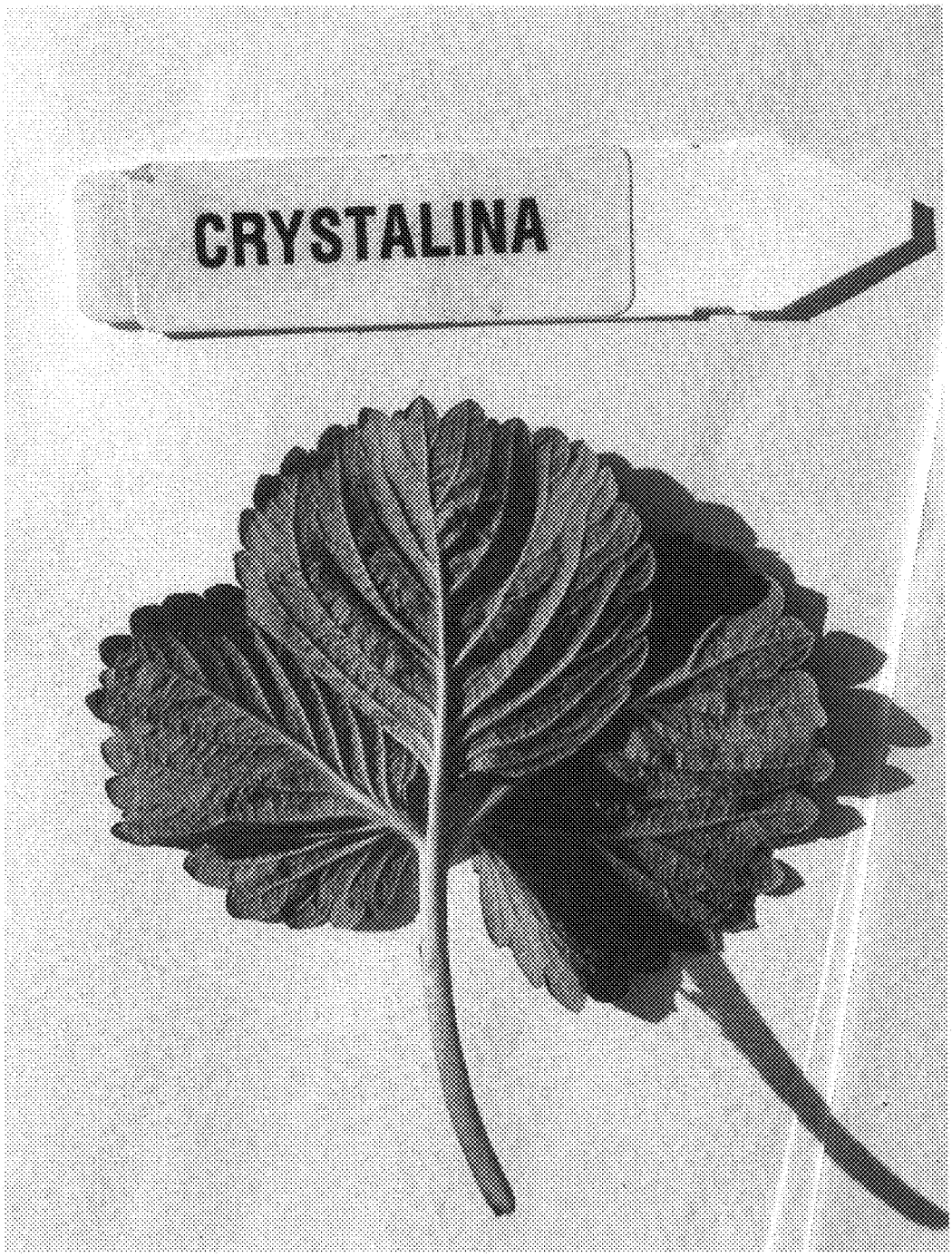
FIG. 11 shows the underside of a 'CRYSTALINA' leaflet.
Figure 12:
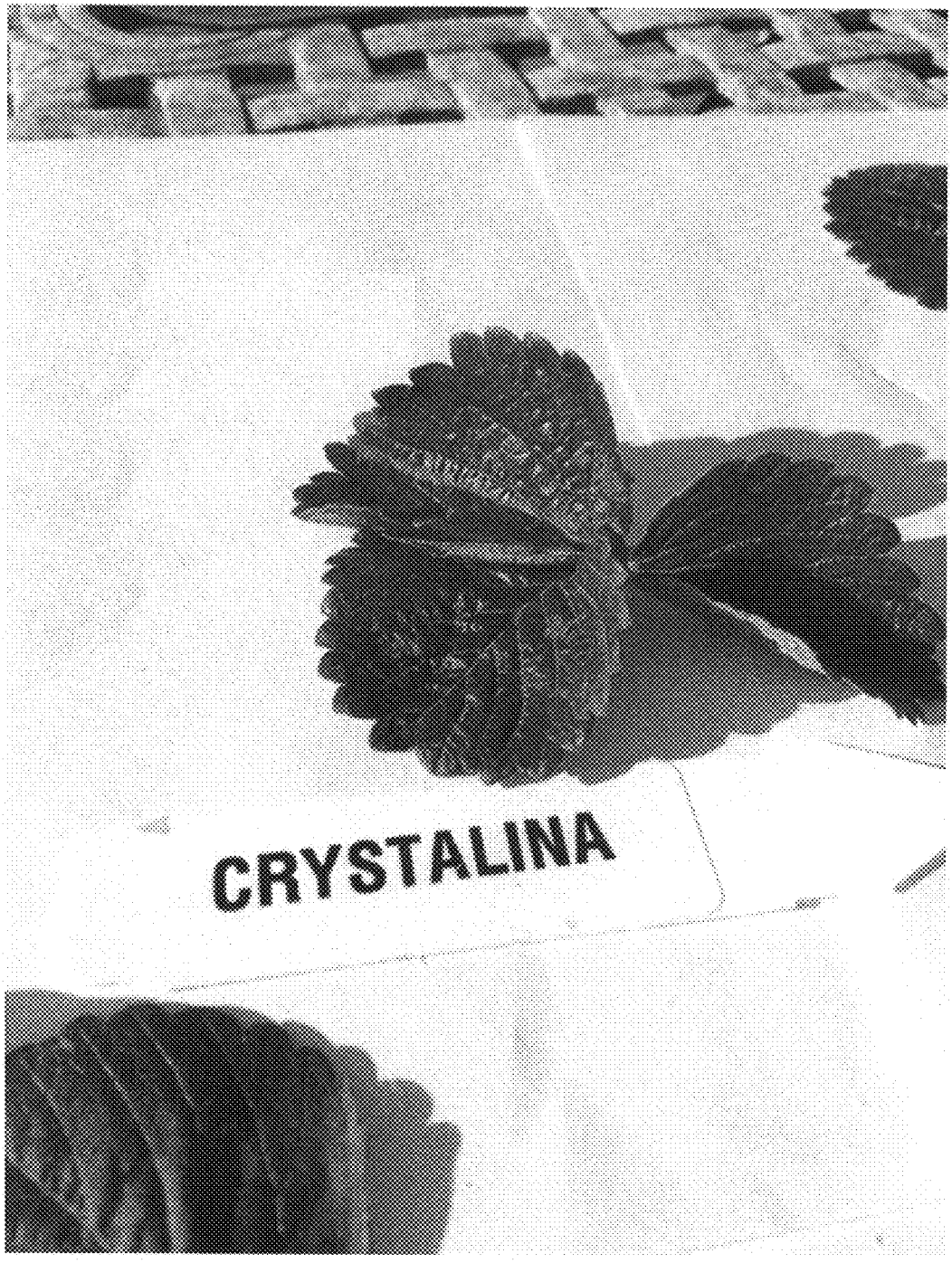
FIG. 12 shows a trifoliate concave overlapping 'CRYSTALINA' leaflet.
Figure 13:
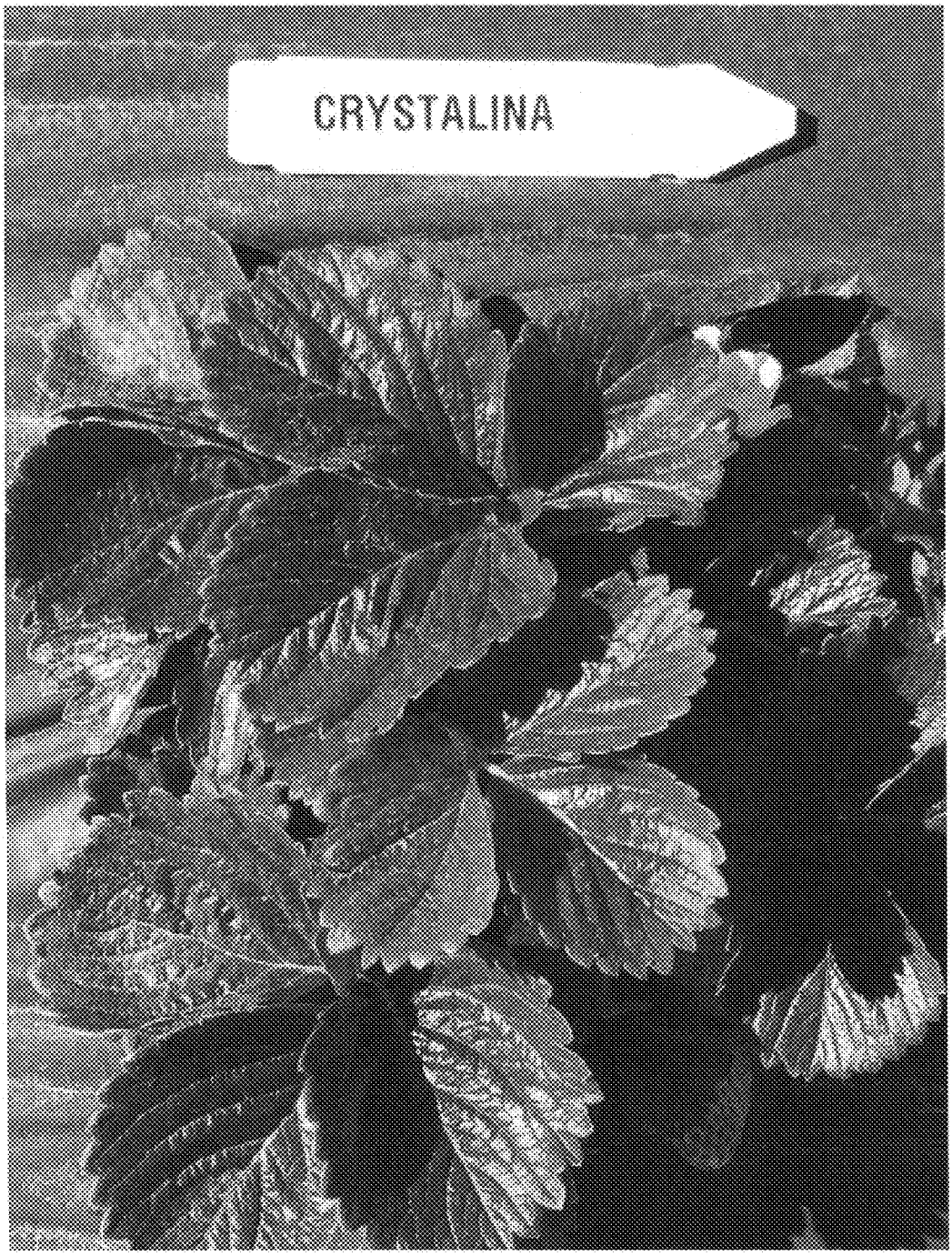
FIG. 13 shows the variable leaflet overlap pattern of 'CRYSTALINA'.
Figure 14:
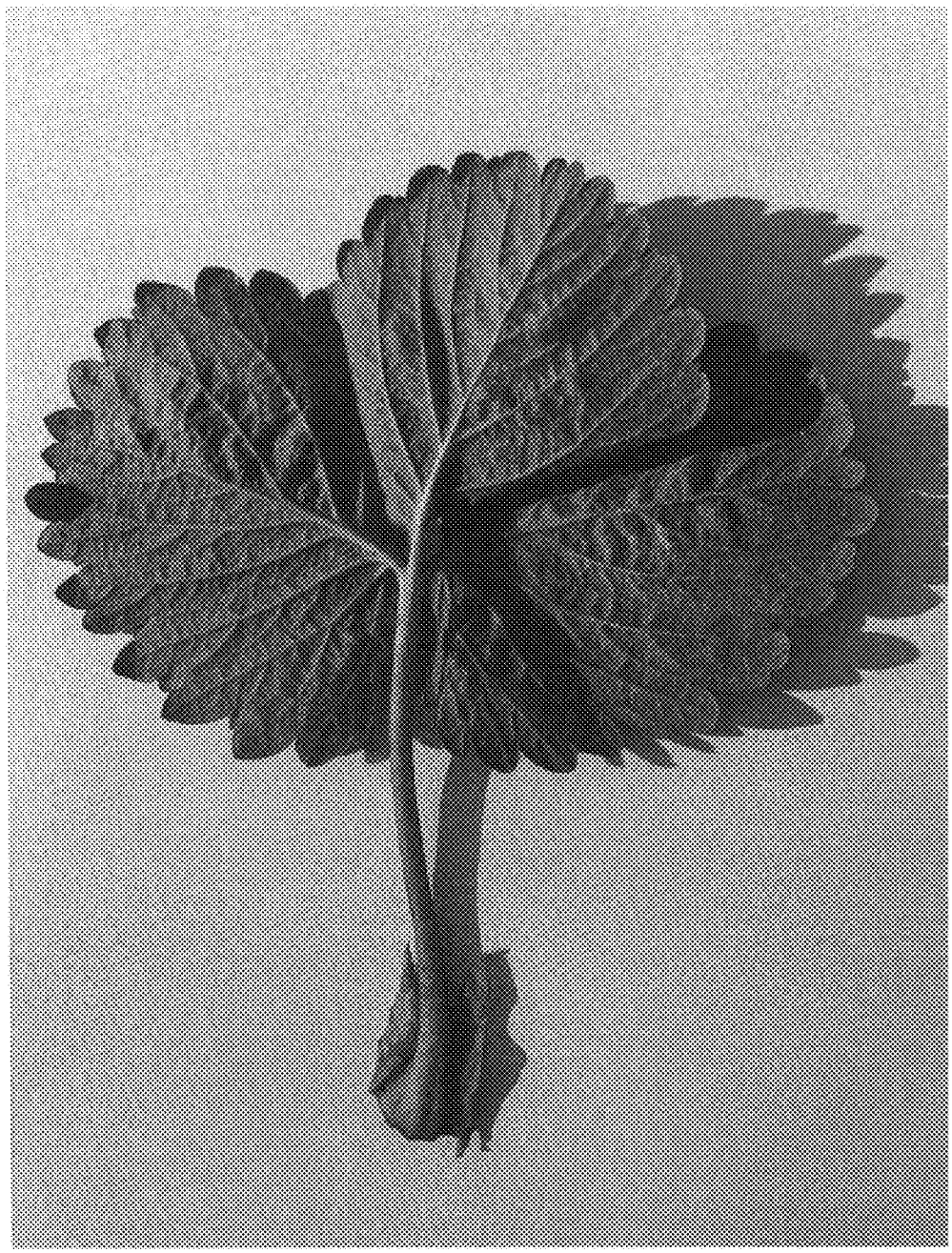
FIG. 14 shows the stipule of a 'CRYSTALINA' leaflet.
Figure 15:
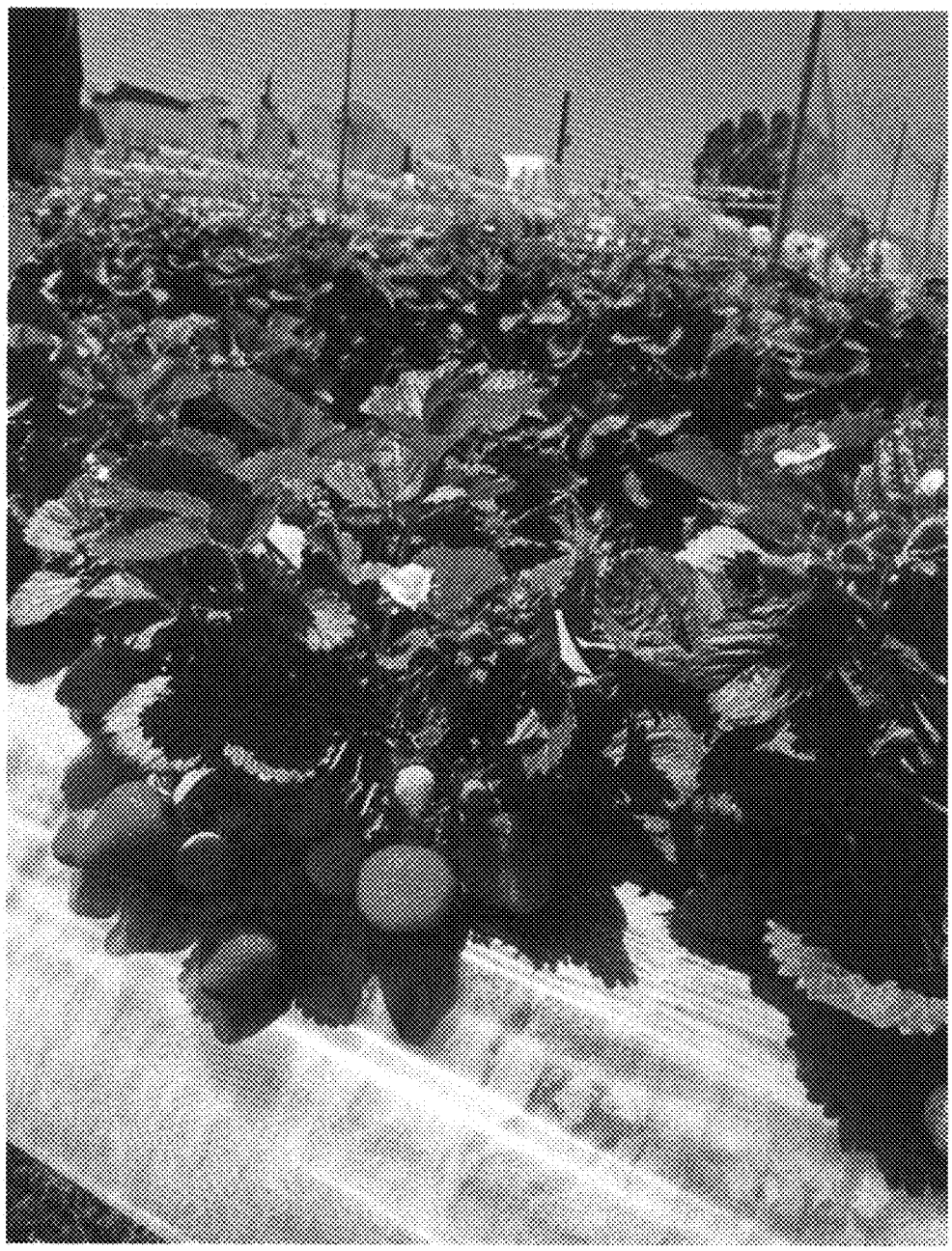
FIG. 15 shows the early season fruiting habit of 'CRYSTALINA'.

'CRYSTALINA' has not been observed under all possible environmental conditions, and the phenotype may vary significantly with variations in environment. The following observations, measurements, and comparisons describe this plant as grown at California, when grown in the field, unless otherwise noted. As stated above, the color determination is in accordance with The Royal Horticultural Society Colour Chart, 1995 Edition, except where general color terms of ordinary dictionary significance are used. Plants for the botanical measurements in the present application are annual plants.

Botanical classification: 'CRYSTALINA' is a fertile hybrid derived from a cross.

Common name: garden strawberry

General Description:

Plant habit: moderate, coastal climates

The following description is applied to our plants that are 7 months old as of the time of the measurements.

Classification:

*Species.*—*Fragaria×ananassa.*
*Common name.*—Garden Strawberry.
*Denomination.*—'CRYSTALINA'.

Parentage:

*Female parent.*—'103904'.
*Male parent.*—'103926'.

Plant:

*Height.*—13.6 cm.
*Diameter.*—19.4 cm.
*Habit.*—Globose, upright.
*Density.*—Medium.
*Vigor.*—Strong.

Terminal leaflet:

*Length.*—6.4 cm.
*Width.*—7.4 cm.
*Length/width ratio.*—0.87.
*Shape in cross-section.*—Concave.
*Blistering.*—Low.
*Glossiness.*—Medium.
*Average number of leaflets.*—Exactly 3.
*Color above.*—Dark Green (RHS 137A).
*Color below.*—Green (RHS 139C).
*Shape.*—Orbicular.
*Margin.*—Crenate to Serrate.
*Venation pattern.*—Reticulate.

Petiole:

*Length.*—7.0 cm.
*Width.*—5.1 mm.
*Color.*—Yellow Green (RHS 145A).

Petiolule:

*Length.*—10.4 cm.
*Width.*—2.7 mm.
*Color.*—Yellow Green (RHS 145A).

Stolon:

*Average daughters/plant.*—About one.
*Diameter.*—3.6 mm.
*Color.*—Dark Purple Red (RHS 53A).

Inflorescence:

*Position relative to foliage.*—At same level.
*Average petals/flower.*—6.5.
*Petal length.*—15.7 mm.
*Petal width.*—15.8 mm.
*Petal length/width ratio.*—0.99.
*Petal shape/base.*—Orbicular.
*Petal apex.*—Round.
*Petal margin.*—Entire.
*Petal spacing.*—Slightly overlapping.
*Petal color.*—White (RHS 157B).
*Corolla.*—30.8 mm.
*Sepal length.*—20 mm.
*Sepal width.*—10.5 mm.
*Sepal length/width ratio.*—1.90.
*Sepal color.*—Dark Green (RHS 137A).
*Calyx.*—53.8 mm (Diameter relative to corolla: Larger).
*Peduncle.*—9.0 cm.
*Bract frequency.*—Low.

Fruit:

*Fruit truss attitude.*—Prostrate.
*Fruit truss length and diameters.*—Average length of 89.1 mm with average thickness of 7.05 mm.
*Relative size.*—Large.
*Fruit length.*—40.7 mm.
*Fruit width.*—39.1 mm.
*Fruit length/width ratio.*—1.04.
*Surface color.*—Red (RHS 45A).
*Flesh color.*—Orange Red (RHS 41B).
*Core color.*—White (RHS 155C).
*Shape.*—Predominately conical.
*Average weight/fruit.*—22.5 g.
*Average weight/plant.*—103.5 g.
*Hollow core length.*—30.3 mm.
*Hollow core width.*—10.1 mm.
*Hollow core length/width ratio.*—3.0.
*Insertion of achenes.*—Indented.
*Average achenes/fruit.*—213.
*Firmness of flesh.*—Medium.
*Glossiness.*—Medium.
*Sweetness.*—Medium.

The center leaflet of 'CRYSTALINA's' trifoliate leaflets has a length to width ratio of 0.94 (6.25 cm/6.65 cm). Leaflets of Crystalina are concave as well as overlapping. Viewed from the topside of the trifoliate leaflets, the two outer leaflets (left leaflet and right leaflet) overlapp with the lower third of the middle leaflet of the trifoliate by 1 centimeter at the greatest dimension of the overlap. The longitudinal dimension of the overlapping leaf measures 4.55 centimeters from the base of the leaflet out to the point where the two leaves are not overlapped. The two outer leaflets of the trifoliate are each asymmetrical in shape where the width dimension of the leaflets measured at the widest distance is a diagonal line that crosses the leaflet near a 45 degree angle relative to the line of the center vein of the leaflet. The middle leaflet of the trifoliate has similar but less pronounced asymmetrical shape.

The left leaflet length to width ratio is 6.5 cm/7.1 cm=0.9285. The leaflet asymmetry of shape of the left leaflet is observed when a comparison is made between the widest dimension of the right hemisphere of the left leaflet which is 3.25 cm and describes a point on the leaflet midrib that is located 3.1 cm above the base of the left leaflet midrib whilst compared to the widest dimension of the opposing hemisphere of the left leaflet which is 3.65 cm wide and the widest width vector of the right hemisphere of the left leaflet intersects the midrib 2.85 cm from the base of the midrib of the left outer leaflet (top of leaf view) of the trifoliate leaflets.

The right outer leaflet length to width ratio is 6.62 cm/7.1 cm=0.932. The right outer leaflet of the trifoliate leaflets differs from the left outer leaflet in its shape. The widest point of the left hemisphere of the right leaflet is 3.3 cm as measured on a vector perpendicular to the midrib and the widest dimension vector intersects the right leaflet midrib at 3.1 cm above the base of the midrib whilst compared to the widest dimension of the opposing hemisphere of the right leaflet which is 3.95 cm wide and the widest width vector of the right hemisphere of the left leaflet intersects the midrib 1.85 cm from the base of the midrib of the right outer leaflet (top of leaf view) of the trifoliate leaflets.

The overlapping of the leaflets was observed to be variable with cases where the middle leaflet dominates the outer leaflet and cases where the outer leaflets dominate the slightly smaller middle leaflet. The expression of the shape of the scallops of the margin of the leaflet of 'CRYSTALINA' is not uniform, with instances of a single small scallop or a pair of small scallops surrounded by series of larger scallops, some sharply pointed and others somewhat rounded. The measured dimension from one scallop to the next gives an array of distances between the topmost points of the scallops measured from left to right (top of leaf view) covering both sides of the apex of the middle leaflet. From the first scallop of each side of the leaflet's dominant outer leaflet overlap points are: 13, 12.5, 7, 7, 11.5, 9, 7, 10, 7, 8, 9, 14, 12.5. The leaflets of 'CRYSTALINA' are stiffer and thicker than the leaflets of strawberry varieties 'GINZA' (U.S. Plant Pat. No. 23,934) and 'CUPCAKE' (U.S. Plant Pat. No. 23,956), which are both commercial strawberry varieties adapted to the same general growing region as 'CRYSTALINA'.

The stipules are a translucent light green with some minimal light brownish color near the base. A dimension of 35 mm was measured from the base of the stipules to each of the two thin tissue blade-like bilateral pointed tops of 'CRYSTALINA's' stipules. The two narrow pointed tops of the stipules are dimensionally 19.5 mm from each other and the two stipule pointed tops are 10.5 mm and 12 mm, respectively, from the longitudinal center of the petiole. The dimension from the points of the tops of the stipule for each is 21.5 mm as measured along the inner edge of the stipule from the topmost point to the bottom of the V notch that is located where the two top parts join together at a point 21 mm above the base of the stipule. At the base of the stipule there is an 18.5 mm wide and 9 mm thick longitudinally curved whitish color tissue where the stipule connects to the axial crown of the plant at its base and becomes the fruit bearing petiole at a point visible on the opposite side of the stipule/petiole structure nearly opposite the previously described notch where the thin light green blade-shaped tissue form a V notch. On either side of the thicker curved base tissue there are 9.5 mm and 10.5 mm wide strips of the light green thin translucent tissue that extends up 35 mm and become the two separated pointed tops of the stipule.

The first of season florescence and fruiting structure are singular in structure with one flower or one ripe or ripening fruit per petiole.

The achene color of 'CRYSTALINA's' fruit is light yellow green to green and red to reddish brown.

'CRYSTALINA's' fruit is harvested two times per week for about 24 weeks beginning in mid-March in the central coast region of California.

The invention claimed is:

1. A new and distinct cultivar of strawberry plant named 'CRYSTALINA' substantially as shown and described herein.

* * * * *